United States Patent
Helmy et al.

(10) Patent No.: US 11,911,428 B2
(45) Date of Patent: Feb. 27, 2024

(54) MEDICINAL AMBROSIA MARITIMA EXTRACTS

(71) Applicants: Sherine Hassan Abbas Helmy, Alexandria (EG); Layla Mohamed Fakhr El-Din El-Sawy, Alexandria (EG); Mohamed Gomaa Seadawy Khamis, Sinnuris (EG)

(72) Inventors: Sherine Hassan Abbas Helmy, Alexandria (EG); Layla Mohamed Fakhr El-Din El-Sawy, Alexandria (EG); Mohamed Gomaa Seadawy Khamis, Sinnuris (EG)

( * ) Notice: Subject to any disclaimer, the term of this patent is extended or adjusted under 35 U.S.C. 154(b) by 0 days.

(21) Appl. No.: 17/317,974

(22) Filed: May 12, 2021

(65) Prior Publication Data

US 2022/0362321 A1 Nov. 17, 2022

(51) Int. Cl.
*A61K 36/28* (2006.01)
*A61K 31/365* (2006.01)
*A61P 31/14* (2006.01)

(52) U.S. Cl.
CPC ............ *A61K 36/28* (2013.01); *A61K 31/365* (2013.01); *A61P 31/14* (2018.01); *A61K 2236/35* (2013.01); *A61K 2236/39* (2013.01)

(58) Field of Classification Search
None
See application file for complete search history.

(56) References Cited

PUBLICATIONS

"SARS"—https://www.who.int/health-topics/severe-acute-respiratory-syndrome#tab=tab_3—accessed Jan. 2023.*
"MERS-CoV" https://www.who.int/health-topics/severe-acute-respiratory-syndrome#tab=tab_3—accessed Jan. 2023.*
"COVID-19: Prevention and risks"—https://www.canada.ca/en/public-health/services/diseases/2019-novel-coronavirus-infection/prevention-risks.html—accessed Jan. 2023.*
Geraghty (Viruses (2021), vol. 13, p. 667).*
Badawy, M.; Abdelgaleil, S. A. M.; Suganuma, T.; Fuji, M. Antibacterial and biochemical activity of Pseudoguaianolide Sesquiterpene isolated from Ambrosia maritima against plant pathogenic bacteria. 2014, Plant Protect. Sci. 50(2), 64-69.
Hayden, F. G.; Cote, K. M.; Douglas, Jr. R. G.; Plaque inhibition assay for drug susceptibility testing of influenza viruses. 1980, Antimicrobial Agents and Chemo., 17(5), 865-870.
Mosmann, T. Rapid colorimetric assay for cellular growth and survival: application to proliferation and cytotoxicity assays. 1983, J. Immunological Methods, 65(1-2), 55-63.

* cited by examiner

*Primary Examiner* — Susan Hoffman
(74) *Attorney, Agent, or Firm* — Boulware & Valoir, PLLC (57) ABSTRACT

Phytoceutical compositions from polar organic extracts of the *Ambrosia maritima* plants and uses thereof for treatment of coronavirus infections are described.

10 Claims, 4 Drawing Sheets

MEDICINAL AMBROSIA MARITIMA EXTRACTS

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE DISCLOSURE

The disclosure relates generally to methods and compositions for treating coronaviruses, and in particular to the field of phytoceutical compositions for the treatment of coronaviruses.

BACKGROUND OF THE DISCLOSURE

Plant based therapeutics have been known and used since ancient times, and still provide between 30-40% of our new drug candidates each year. The complexity of the components contained within plants are not fully understood and it is appreciated that an in-depth biochemical analysis of the components of plants as they are found e.g., in leaves, stems, and the like, may continue to reveal valuable therapeutic compounds for the treatment of various illnesses as diverse as microbial infections or migraines.

Recently, there has been considerable interest in searching the phytochemical properties of many long-ago discovered plants to determine their potential pharmaceutical benefits, most particularly, on secondary metabolites. In addition to the primary metabolism necessary for life, plants have a secondary metabolism that generates compounds, which aid in their growth and development. A common role of secondary metabolites is defense mechanisms to fight off animals, pest and pathogens. These compounds have become the focus of much pharmacological interest.

One plant family of interest for natural therapeutics is the *Asteraceae* (or Compositae). This family has a remarkable ecological and economical importance and is present from the polar regions to the tropics, colonizing all available habitats, though it is most commonly found in arid areas. *Asteraceae* has been regarded as a promising family of plants because of the amount and variety of active compounds produced by secondary metabolism. Some commonly known uses of the *Asteraceae* are in herbal products such as teas (Chamomile, *Echinacea*) or potpourri (Marigold). However, there is also growing evidence that Asteranceae contains secondary metabolites that can be beneficial in the treatment of many diseases.

Coronaviruses, a genus in the family of Coronaviridae, are large, enveloped, positive-strand RNA viruses. Coronaviruses derive their name from the fact that, under electron microscopic examination, each virion is surrounded by a "corona," or halo resulting from the protrusion of spiked proteins, also called peplomers, on the surface. Most coronaviruses infect only one host species and have been identified in mice, rats, chickens, turkeys, swine, dogs, cats, rabbits, horses, cattle and humans, although crossovers are possible.

Figure 3A:
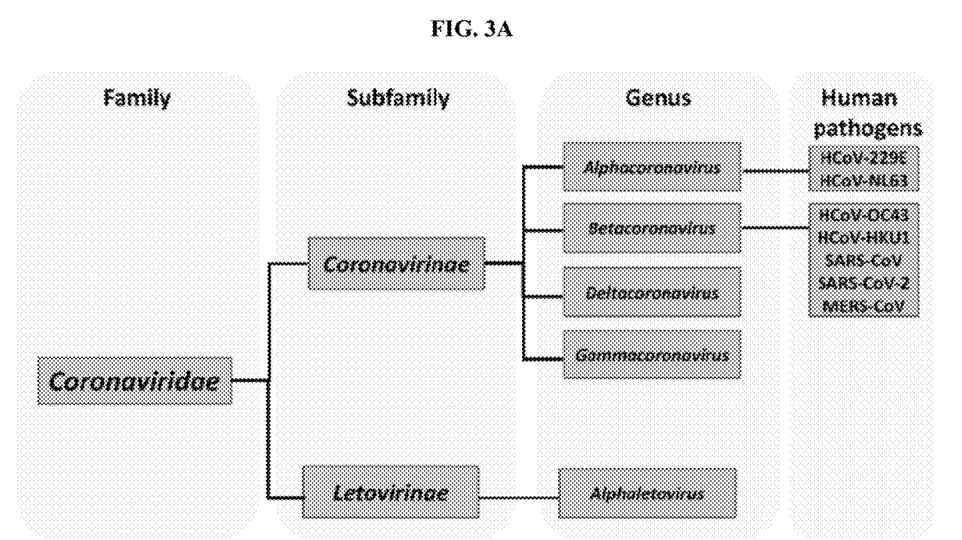
FIG. 3A. Coronovidea family with known human pathogens.
Figure 3B:
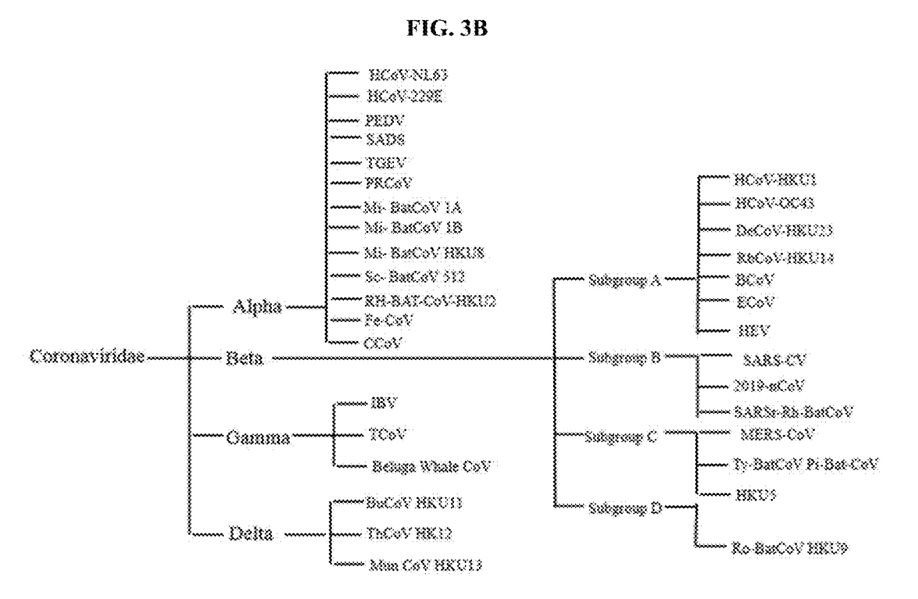
FIG. 3B. Coronovidea family with human and animal pathogens.

The family Coronaviridae is organized in 2 sub-families, 5 genera, 26 sub-genera, and (at least) 46 species. By "coronaviruses" herein we include the entire subfamily corovirinae, which includes Alpha-, Beta-, Gamma-, and Delta-coronaviruses. FIG. 3A shows the known human pathogens, and FIG. 3B shows a more complete (but not exhaustive) list. It is included herein because the coronavirus is sometimes zoonotic and may become human pathogens under the right conditions. In addition, the inventive compositions and methods can be used in non-human animals as well, such as domestic mink which are now heavily infected with SARS-CoV-2.

Six species of human coronaviruses are known, with one species subdivided into two different strains, making seven strains of human coronaviruses altogether. Four human coronaviruses produce symptoms that are generally mild, even though it is contended they might have been more aggressive in the past:
  Human coronavirus OC43 (HCoV-OC43), β-CoV
  Human coronavirus HKU1 (HCoV-HKU1), β-CoV
  Human coronavirus 229E (HCoV-229E), α-CoV
  Human coronavirus NL63 (HCoV-NL63), α-CoV Three human coronaviruses produce symptoms that are potentially severe:
  Middle East respiratory syndrome-related coronavirus (MERS-CoV), β-CoV
  Severe acute respiratory syndrome coronavirus (SARS-CoV-1), β-CoV
  Severe acute respiratory syndrome coronavirus 2 (SARS-CoV-2), β-CoV Coronaviruses can cause diseases ranging from the common cold to gastroenteritis and respiratory tract diseases. In recent years, coronaviruses have been the source of many outbreaks, starting with the severe acute respiratory syndrome (SARS) coronavirus (SARS-CoV-1) epidemic in 2003, which killed about 10% of those infected. The rapid transmission and high mortality rate made SARS-CoV-1 a global threat for which no efficacious therapy was available. Since then, the study of coronavirus molecular biology was given a very high priority in order to develop effective strategies to prevent and control coronavirus infections, though no proven vaccine or antiviral therapy exists as of this application. Subsequent outbreaks of Middle East respiratory syndrome coronavirus (MERS-CoV), or MERS, which had a 35% death rate, and the on-going global pandemic of severe acute respiratory syndrome coronavirus 2 (SARS-CoV-2), which causes COVID-19 and has a 1.8% death rate in the US, have proved that much work still needs to be done.

Even though a number of vaccines have been produced for COVID-19, there still exists a need for the development of effective therapies to treat severe diseases caused by coronaviruses, both those currently known and those yet to be discovered. The ideal treatments would also have prophylactic effect, thus allowing the prevention of infection in first responders, the elderly and those patients exposed to infection, but not yet sick.

SUMMARY OF THE DISCLOSURE

Disclosed herein are compositions comprising several pharmaceutical compounds extracted from a member of the plant family *Asteraceae* and methods of using these compounds for coronavirus infection prevention and treatment, including betacoronavirus infection. These compounds have been proven efficacious against COVID-19 and MERs in in vitro laboratory models.

In more detail, these pharmaceutical compounds target the spike protein protruding from the coronavirus envelop, thus reducing or eliminating its ability to engage with angiotensin-converting enzyme 2 (ACE2) and enter a host cell. Further, the pharmaceutical compounds have been shown to target the main protease and the RNA-dependent RNA polymerase on coronaviruses, which can lead to a reduction or elimination of viral gene expression and replication.

The present compounds relate to an extract of pharmaceutical potential derived from the organic fraction of whole Asteracea plants, including, but not limited to *Ambrosia maritima*. *Ambrosia maritima* is richly branched and has grey-hairy aromatic fragrant leaves and green, solid and striated stems with faint ridges. This plant can be found mainly in the coastal strip of North Africa's Mediterranean region and along the muddy canal banks of the Nile in Egypt and Sudan.

Many studies on *Ambrosia maritima* have shown that it has some pharmacological action. A study conducted by Alard et al. showed no toxic signs could be detected after oral administration of 5 g/kg of dried leaves of the plant as a powder nor as a methanolic extract, nor after the incorporation of 50,000 ppm powdered leaves in the feed for a duration of 4 weeks. Further, no mutagenic effect could be detected in mutagenicity test using *Salmonella typhimurium* strains TA97, TA 98, TA1538, TA100 and TA1535 (Alard 1991).

*Ambrosia maritima* has been shown to kill the intermediate host of Schistosomiasis and Fascioliasis (both parasitic infections) at a concentration of 3000 mg/L in water streams (M. F. El-Sawy 1977 and 1986). Some compounds within *Ambrosia maritima* have considerable cytotoxic effect (Abdallah 1991) and antimicrobial activity (Badawy 2014). Further, *Ambrosia maritima* has shown use as a muscle relaxant of the intestine, uterus and blood vessels; to increase urine output/day; and, to help to decrease body weight.

*Ambrosia maritima* contains several compounds with possible pharmacological effects, such as chloroambrosin, ambrosin, damsin, neoambrosin, farnserin, hymendin, hymenin, stamonin-b, anhydrofranserin, triterpenes, s-amyrin, apigenin, coumarins, sterols, β-sitosterol, tannin, volatile oil, carvone, camphor, caryophyllene, cineole, salts and other sesquiterpene lactones. However, the present methods focus on the use of sesquiterpene lactones.

Sesquiterpene lactones (SL) are compounds found in the organic fraction of the plant extract. The SLs in this organic extract are mostly bifunctional sesquiterpene lactones and show the ability to directly bind to diverse proteins with high affinity. We have found that they react specifically with viral proteins that play a prominent role in a coronavirus's entry, replication and expression process. The α,β-unsaturated ketone moieties of the plant derived sesquiterpene lactones behave as Michael acceptors in spontaneous reactions with cysteine sulfhydryl groups on various viral proteins under physiological conditions to inhibit the viral proteins' function.

Figure 1A:
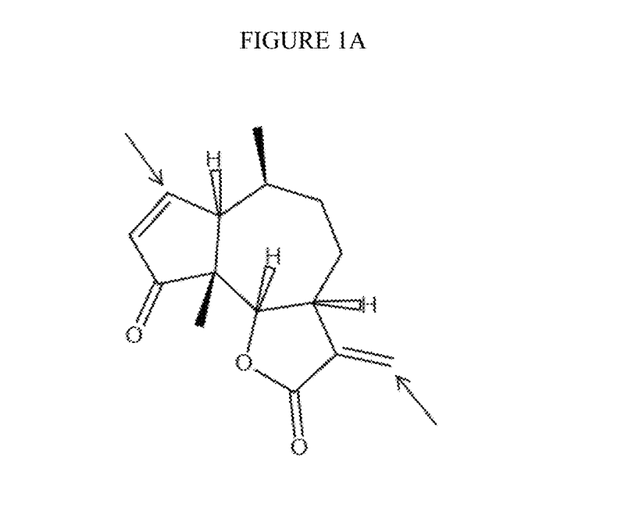
FIG. 1A. Chemical structure of exemplary SL Ambrosin with arrows pointing to the Michael reaction points.
Figure 1B:
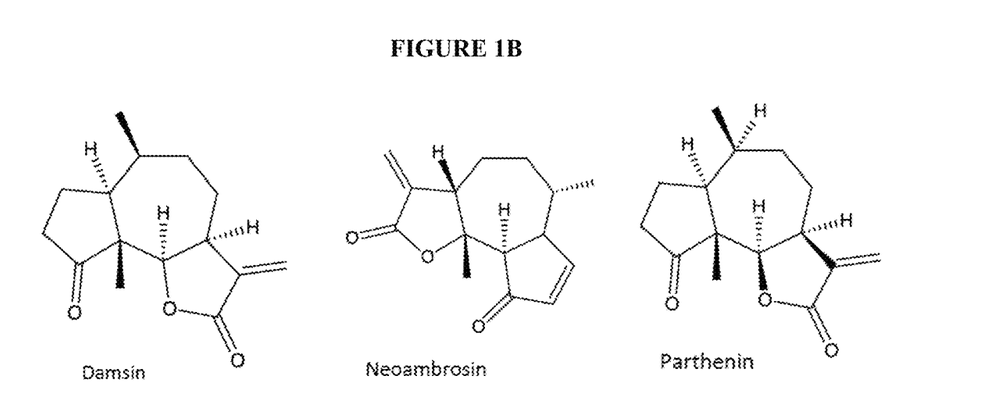
FIG. 1B. Chemical structure of three additional exemplary SLs found in *Ambrosia* plants.

FIG. 1A displays a typical bifunctional sesquiterpene lactone with arrows pointing at the two Michael acceptor sites, which allows the SL to act as a crosslinker between two protein cysteine side chains. However, several of the SLs found in *Ambrosia maritima* contain two or more Michael acceptor sites in the same molecule. FIG. 1B displays three other SLs found in extracts from *Ambrosia* plants.

Many different SLs are present in the *Ambrosia maritima* organic extract, including ambrosin, damsin, neoambrosin, parthenin, helenalin, tribromoambrosin and the like. The present methods preferably use the entire spectrum of SLs found in the organic extract of the whole plant for treatment. However, with time and identification of the main active ingredients, it will be possible to purify individual SLs for treatment or to synthesize specific SLs by organic chemistry methods and then optimize the preparation for specific uses. While it is expected that most coronaviruses will respond to the entire spectrum of SLs found in an organic extract from a whole *Ambrosia* plant, some coronaviruses may also benefit from treatment with the individual SLs or a subset of SLs found in the organic extract. The selection of individual SLs from the whole plant extract can be tunable, thus allowing the purified individual SLs to be combined in ratios not normally found in the organic extract. In some embodiments, the presently disclosed compositions have four purified individual SLs: ambrosin, damsin, parthenine, and neoambrosin.

In the present methods, the *Ambrosia maritima* plant is mixed with an organic solvent such as acetonitrile, methanol, ethanol, isopropanol, ether, ethyl acetate, acetone or mixtures thereof to extract the SLs. A polar organic solvent is preferably used.

Generally, the mixture of plant tissue and polar organic solvent will be left to stand at room temperature, thereby allowing the extraction to take place. Alternatively, the plant tissue may be exhaustively extracted with a polar organic solvent in a Soxhlet apparatus or the like.

The plant tissue may be fresh, frozen or dried and may be in comminuted form. The whole plant is preferably used as it will have a different profile of active ingredients than the leaves or stems of the plant.

The solvent extract is then generally separated from the plant tissue and the solvent removed from the extract by drying or precipitation and the like. Following removal of the solvent, the remaining primary extract, also called a crude extract, may be further purified by known techniques such as size exclusion chromatography, ion exchange chromatography, HPLC, precipitation, crystallization, further solvent extraction, and reverse phase chromatography, and the like. The remaining plant tissue may be further extracted using the same or an alternative solvent.

In some embodiments, the crude extract undergoes chromatographic separation using a second organic solvent that is preferably non-polar to purify and fractionate each SL. Two or more fractions can optionally be combined in various ratios for administration to a patient.

Figure 1C:
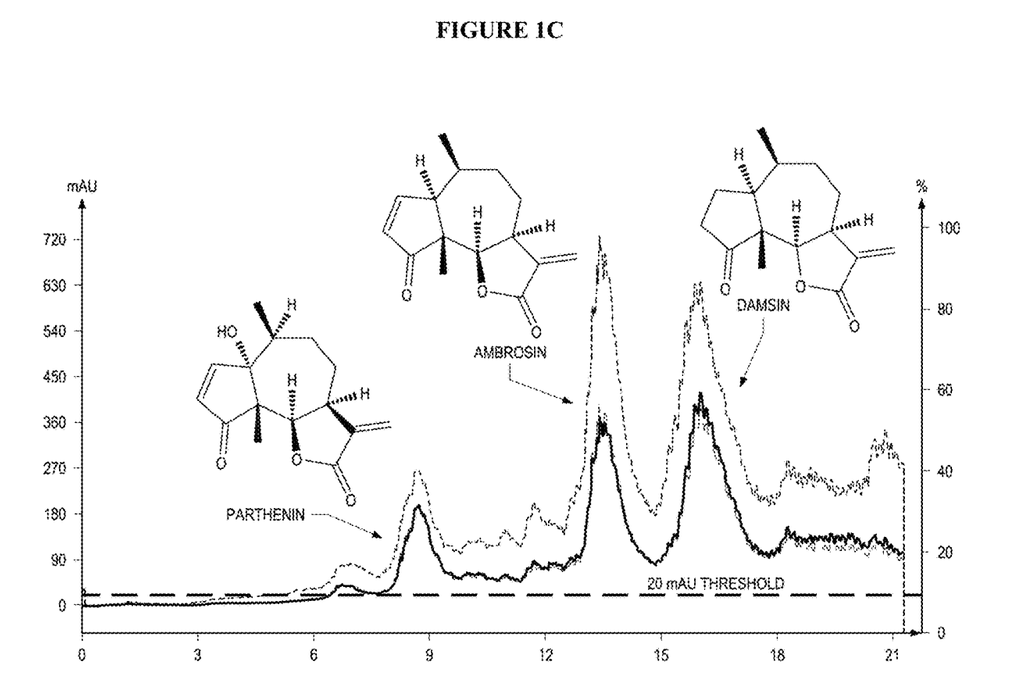
FIG. 1C. Chromatographic fingerprints of sesquiterpene lactones extracted from *Ambrosia maritima*.

FIG. 1C displays the chromatographic fingerprint of the SLs in the organic extract of *Ambrosia maritima*. The active ingredient or ingredients of the polar organic extract of plant material can be used as is, or are preferably formulated with known pharmaceutically acceptable carriers, diluents and/or excipients.

For example, gelatin capsules containing dried organic and/or purified compounds of the extract can be produced containing a suitable dose of the active ingredient(s). Optionally, packets containing the dried extract together with sweeteners and/or flavorants and excipients such as anti-agglomeration agents, can be provided for mixture with e.g., hot fluids, to be taken orally. The extract can also be formulated with solid carriers for pressing into pill or tablet forms, especially with delayed release excipients and/or coatings for formulating once a day pill/tablet form. Other pharmaceutical formulations could be liquid or solid carriers and/or excipients to be administered orally.

It may also be possible to prepare forms of the active ingredients suitable for non-oral routes of administration, such as intravenous, inhalational, buccal, sublingual, nasal, dermal, suppository or parenteral dosage forms.

In more detail, the invention may comprise one or more of the following:

A method of treating a patient infected with a coronavirus, comprising administering an effective amount of any composition described herein to a patient with a coronavirus infection.

A method of treating a patient infected with a betacoronavirus, comprising administering an effective amount of any composition described herein to a patient with a betacoronavirus infection.

A method of treating Middle East respiratory syndrome coronavirus (MERS), comprising administering an effective amount of any composition described herein to a patient with a MERS infection.

A method of treating severe acute respiratory syndrome coronavirus 1 (SARS-CoV-1), comprising administering an effective amount of any composition described herein to a patient with a SARS-CoV-1 infection.

A method of treating severe acute respiratory syndrome coronavirus 2 (COVID-19), comprising administering an effective amount of any composition described herein to a patient with a COVID-19 infection.

A method of preventing a coronavirus infection in a patient comprising administering an effective amount of any of the compositions described herein to a patient exposed to a coronavirus or to a patient that may be exposed. Preventatives can be used in anyone.

A method of preventing a betacoronavirus infection in a patient comprising administering an effective amount of any of the compositions described herein to a patient exposed to a betacoronavirus.

A method of preventing Middle East respiratory syndrome coronavirus (MERS) infection, comprising administering an effective amount of any of the composition described herein to a patient exposed to MERS.

A method of preventing a severe acute respiratory syndrome coronavirus 1 (SARS-CoV-1) infection, comprising administering an effective amount of any of the composition described herein to a patient exposed to SARS-CoV-1.

A method of preventing a severe acute respiratory syndrome coronavirus 2 (COVID-19) infection, comprising administering an effective amount of any of the composition described herein to a patient exposed to COVID-19. The effective amount of the composition is administered daily for at least 5 days to 2-3 weeks.

A method of treating a coronavirus infection, comprising administering an effective amount of a composition comprising a polar organic extract of a whole *Ambrosia maritima* plant together with a pharmaceutically acceptable carrier to a patient with a coronavirus infection. In particular, the coronavirus infection is caused by a betacoronavirus such as MERS, SARS-CoV-1, and COVID-19. The effective amount of the composition is administered daily for at least 5 days to 2-3 weeks. Further, the organic extract comprising at least one sesquiterpene lactone is protein free, thus is less pyrogenic.

A method of treating a coronavirus infection, comprising administering an effective amount of a composition comprising sesquiterpene lactones extracted from *Ambrosia maritima* together with a pharmaceutically acceptable carrier to a patient with a coronavirus infection. In particular, the coronavirus infection is caused by a betacoronavirus such as MERS, SARS-CoV-1, and COVID-19 and the effective amount of the composition is administered daily for at least 5 days to 2-3 weeks.

A method of reducing coronavirus entry into a host cell comprising administering an effective amount of a composition comprising sesquiterpene lactones extracted from a whole *Ambrosia maritima* plant together with a pharmaceutically acceptable carrier to a patient with a coronavirus infection or exposure to coronavirus.

A method of treating or preventing a coronavirus infection involving (1) preparing a sesquiterpene lactone-containing extract for pharmaceutical by treating an *Ambrosia maritima* plant with a polar organic solvent in which at least one said sesquiterpene lactone is soluble, evaporating the polar organic solvent to produce a crude extract, running or passing the crude extract through a chromatographic separation using a second organic solvent to obtain a clean extract of the sesquiterpene lactone(s), and collecting fractions of one or more individual sesquiterpene lactone(s) to form a sesquiterpene lactone-containing extract; (2) adding a pharmaceutically acceptable carrier to the sesquiterpene lactone-containing extract to form a pharmaceutical composition; and (3) administering an effective amount of the pharmaceutical composition to a patient already exposed or subject to possible exposure to a coronavirus or a patient with a coronavirus infection.

Any of the methods described herein, wherein the coronavirus infection is caused by an Alpha-, Beta-, Gamma-, and Delta-coronaviruses. Alternatively, any of the methods described herein, wherein the coronavirus infection is caused by Human coronavirus OC43, Human coronavirus HKU1, Human coronavirus 229E, Human coronavirus NL63, Middle East respiratory syndrome-related coronavirus, Severe acute respiratory syndrome coronavirus, or Severe acute respiratory syndrome coronavirus 2.

Any of the above methods of treatment, wherein the patient is a human or an animal. Animals may include any animal that contracts coronaviral diseases, and especially includes mammals such as mink, dogs, cats (including the large cats such as tigers), monkeys and other primates, goats and other pets, many of which have already been shown to contract COVID-19.

A pharmaceutical composition comprising a polar organic extract of a whole *Ambrosia maritima* plant together with a pharmaceutically acceptable carrier that can be a pharmaceutical acceptable excipient, buffer, chelator, or delayed release matrix or combinations thereof; any of the composition herein described in gelatin capsule form, pill form, or liquid form for oral use.

A pharmaceutical composition comprising a polar organic extract of a whole *Ambrosia maritima* plant together with a pharmaceutically acceptable carrier that can be a pharmaceutical acceptable excipient, buffer, chelator, or delayed release matrix or combinations thereof; any of the composition herein described in gelatin capsule form, pill form, or liquid form for oral use.

A method of preparing the pharmaceutical composition described, the method comprising comminuting a whole *Ambrosia maritima* plant, extracting an organic soluble component from the comminuted whole

*Ambrosia maritima* plant and adding a pharmaceutically acceptable carrier to said organic soluble component.

A method of preparing the pharmaceutical composition herein, said method comprising comminuting a whole *Ambrosia maritima* plant, extracting an organic soluble component(s) from the comminuted whole plant, purifying the extracted organic soluble compound(s), and adding a pharmaceutically acceptable carrier to said purified organic soluble component(s). The organic soluble component can be obtained using a polar organic solvent.

A method of preparing a sesquiterpene lactone-containing extract for a pharmaceutical composition involving extracting an *Ambrosia maritima* plant with a polar organic solvent in which at least one said sesquiterpene lactone is soluble, evaporating the polar organic solvent to produce a crude extract, running or passing the crude extract through a chromatographic separation using a second organic solvent to obtain a clean (or purified) extract of the sesquiterpene lactone(s), and collecting fractions of the individual sesquiterpene lactone(s). Two or more fractions can optionally be combined in various ratios.

A method of preparing the pharmaceutical composition described, said method comprising comminuting a whole *Ambrosia maritima* plant, extracting an organic soluble component from said comminuted whole *Ambrosia maritima* plant and adding a pharmaceutically acceptable carrier to said organic soluble component; a method of preparing the pharmaceutical composition herein, said method comprising comminuting a whole *Ambrosia maritima* plant extracting an organic soluble component(s) from said comminuted whole plant, purifying the extracted organic soluble compound(s), and adding a pharmaceutically acceptable carrier to said purified organic soluble component(s).

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, "plant matter" refers to any part or parts of the plant taken either individually or in a group (including the whole plant) and is not limited to leaves, flowers, roots and stems.

The term "organic extract," as used herein, refers to a composition prepared by contacting plant material with an organic solvent following procedures such as those described herein. The term encompasses crude extracts, prepared by a simple organic solvent extraction, as well as crude extracts that have been subjected to one or more separation and/or purification steps, including substantially purified and purified active ingredient(s) and concentrates or fractions derived from a crude extract by subjecting the crude extract to one or more additional extraction, concentration, fractionation, filtration, condensation, distillation or other purification step. The plant extract may be in liquid form, such as a solution, concentrate or distillate, semiliquid form, such as a gel or paste, or it may be in solid form, such as in granulate or powder form. The plant matter may be fresh, dried, frozen, or in a comminuted form.

The term "active ingredient" includes one or more active ingredients (e.g., compounds having pharmaceutically efficacy against a coronavirus, preferably against one or more of MERS, SARS-CoV-1, SARS-CoV-2, and other coronavirus infections) isolatable from at least the *Ambrosia maritima* and potentially from other *Ambrosia* species or even other plant families. It includes both synthetic (chemically made) and natural (derived from plants) forms of the active ingredient.

The term "isolated," when used in reference to a compound or compounds having pharmaceutical activity, refers to a form of the active ingredient that is relatively free (at least 25% pure on a dry matter basis) of proteins, nucleic acids, lipids, cell wall, carbohydrates or other materials with which it is naturally associated in a live plant.

The term "concentrated" when used in reference to an active ingredient, refers to a form of the active ingredient that is at least 50% pure when analyzed by HPLC.

The term "substantially purified," when used in reference to an active ingredient, refers to a form of the active ingredient that is at least 75% pure when analyzed by HPLC and preferably >80%, or >85%.

The term "purified," when used in reference to an active ingredient refers to a form of the compound(s) that is at least 90% pure, and preferably is at least 95, 98 or 99% pure when analyzed by HPLC.

The terms "therapy," and "treatment," as used interchangeably herein, refer to an intervention performed with the intention of improving a recipient's medical status and does not necessitate 100% prevention or cure. The improvement can be subjective or objective and is related to the amelioration of the symptoms associated with, preventing the development of, or altering the pathology of an infection, disease, disorder or condition being treated. Thus, the terms therapy and treatment are used in the broadest sense, and include the prevention (prophylaxis), moderation, reduction, and curing of an infection, disease, disorder or condition at various stages. Prevention of deterioration of a recipient's status (i.e. stabilization of the infection, disease, disorder or condition) is also encompassed by the terms. Those in need of therapy/treatment include those already having the infection, disease, disorder or condition as well as those prone to, or at risk of developing, the infection, disease, disorder or condition and prophylactic use in those for whom the infection, disease, disorder or condition is to be prevented, e.g., elderly patients or patients with high-risk comorbidities.

The term "subject" or "patient," as used herein, refers to an animal in need of treatment. The term "animal," as used herein, refers to both human and non-human animals, including, but not limited to, mammals, birds and fish.

As used herein, "effective amount" refers to the amount of organic extract or SL required to confer a biological or meaningful patient benefit, such as the biological or medical improvement sought by a medical doctor or other medical professional or the prevention of infection when used prophylactically. In one aspect, the term "effective amount" is intended to mean the amount of drug that will bring about a biologically meaningful improvement in the subject's viral load and/or symptoms. Doses that exhibit large therapeutic indices are preferred. Effective amounts may vary, as recognized by those skilled in the art, depending, for example, on route of administration, dosage form, inclusion of additional active agents, as well as age, weight, sensitivity, extent of infection, extent of disease, extent of symptoms, and health of the subject.

The term "phytoceutical," as used herein, refers to a plant-comprising composition having therapeutic properties.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| Cys | Cysteine |
| DMEM | Dulbecco's Modified Eagle's Medium |
| HPLC | High-Performance Liquid Chromatography |
| $IC_{50}$ | Half Maximal Inhibitory Concentration |
| kDa | kilo-daltons |
| MERS-CoV | Middle East respiratory syndrome-related coronavirus |
| PFU | Plaque forming unit |
| SARS-CoV-1 | Severe acute respiratory syndrome coronavirus |
| SARS-CoV-2 | Severe acute respiratory syndrome coronavirus 2 |
| SL | Sesquiterpene lactones |

DESCRIPTION OF EMBODIMENTS OF THE DISCLOSURE

The disclosure provides pharmaceutical compositions comprising plant-based compounds and novel methods pertaining to their use in coronavirus infection prevention and treatments. In particular, the polar organic extract from whole *Ambrosia maritima* plants in the *Asteraceae* family is used for prevention and treatment of various coronaviruses infections, including betacoronaviruses. One particular group of components in the organic extract, sesquiterpene lactones, have been found to interfere with viral entry and viral replication pathways. This reduces the viral load and thus infection level, enabling effective prevention and/or treatment.

Extraction Method. Briefly, the extraction uses an organic solvent such as methanol, ethanol and any carbon-based solvents, although a polar organic solvent is preferred. The whole organic extract is dried and chemically fractionated with at least one second organic solvent such as chloroform. The final step is to pool the best fractions and evaporate the second organic solvent(s). The final product can then be used in treatment.

In more detail, the extraction method of *Ambrosia maritima* can be as follows:

1) Dried whole *Ambrosia maritima* plant is powdered using conventional means.

2) The powdered plant is brought into contact with an organic solvent or combination of organic solvents and allowed to contact the plant matter for a predetermined amount of time for the SLs in the dried plant to move into the organic phase. This organic solvent(s) is preferably polar.

3) The organic solvent(s) is then separated from the dried plant material.

4) The organic extract is dried by any known means in the art.

5) The dried extract is chemically fractionated with second organic solvent and fractions rich in the requisite SLs pooled. In some embodiments, the second organic solvent is preferably non-polar, such as chloroform.

6) The second organic solvent (e.g. chloroform) is evaporated, leaving behind the dried, pharmaceutically active components, also referred to as a purified or clean extract.

7) Different concentrations of the active components are used in treating various coronaviruses.

The same extraction steps can be performed for other plants in the *Asteraceae* family.

Other extraction methods can be employed, as suitable for organic soluble components. For example, such methods include, aqueous two-phase systems, acid/base extractions, and the like. To prepare the plant for extraction the plant is typically dried in air with no heat, then further processed by freeze thawing cycles, and/or physically lysed by freezing and thawing before extraction, and the like.

Administration Method. The active ingredient or ingredients of the organic extract of the plant material can be combined with other active ingredients before use, but preferably are used alone. The active ingredient or ingredients of the organic extract of plant material can be used as is, or can be formulated with known pharmaceutically acceptable carriers, diluents and/or excipients.

For example, gelatin capsules containing dried organic extract can be produced containing a suitable dose of the active ingredient(s). Optionally, packets containing the dried extract can be provided for mixture with e.g., hot fluids, to be taken orally. The extract can also be formulated with solid carriers for pressing into pill forms, especially with delayed release excipients for formulating once a day tablet forms or any pharmaceutical form that will be orally administered.

It may also be possible to prepare forms of the active ingredients suitable for non-oral routes of administration, such as inhalational, buccal, sublingual, nasal, suppository or parenteral dosage forms.

The above extract is significantly more stable than the natural product, even in liquid form and especially when formulated with a buffer and a chelator. In fact, stability is predicted to be improved by at least 3, 4, 5 or more orders of magnitude. It is also significantly more concentrated than the natural form, thus providing efficacy without having to consume vast quantities of plant material. Further, the dosage is much more easily controlled with concentrated, partially purified or purified material.

We also used TLC and HPLC to further purify the active ingredient(s) to be further studied and to determine their efficacy, although this work is ongoing. The removal of certain components from the organic extract, through the additional purification step can lead to fewer side effects. *Ambrosia maritima* is a ragweed, which is known for its allergenic effects. Thus, purification of the organic extract will lead to a reduced immune response in humans. In some embodiments, purified material from the organic extract of the *Ambrosia maritima* can serve to improve the ability to interrupt viral entry and replication, and increase stability of the extracted material.

Once the pharmaceutical composition is prepared, the drug is administered daily, preferably 1 to 4 times a day, and most preferably 3 times a day. The amount of purified organic extract, or active ingredients obtained therefrom, in each dose is between 250 mg to 750 mg, or about 500 mg. The length of dosing is at least 5 days, wherein preferred dosing ranges are 5-10 days, 8 to 20 days or 15 to 30 days. Prophylactical use may be longer depending on context and potential side effects, although none are yet known. Daily treatment by oral administration for 1-4 weeks is preferred, but in some cases, the length of time would be extended according to the extent of the coronavirus infection and/or the type of coronavirus.

The pharmaceutical composition can be administered before or after a patient has tested positive for a coronavirus infection. In some embodiments, the pharmaceutical composition can be administered, as a preventative treatment, to a patient exposed to a coronavirus even if the patient is not exhibiting symptoms or testing positive or a patient with no known exposure but in a high risk environment. In other embodiments, the pharmaceutical composition can be administered to a patient testing positive for a coronavirus but not exhibiting symptoms, or for a patient testing positive for a coronavirus and exhibiting symptoms.

The sesquiterpene lactones (SLs) in the present methods can be used to target a variety of coronavirus-specific pathways for entry and replication. Not all pathways involved in a coronavirus's entry into a host cell, a coronavirus infection's growth, and coronavirus infection's progression are known. Thus, the following examples are intended to be illustrative only, and not unduly limit the scope of the appended claims. Those of skill in the art should appreciate that many changes can be made in the specific embodiments which are disclosed and still obtain a like or similar result without departing from the spirit and scope of the disclosure herein. Further, though a betacoronavirus was utilized in the following examples, the present treatment methods are expected to be useful for treatment of most coronaviruses, either alone or in combination with other treatment modalities. In no way should the following examples be read to limit, or to define, the scope of the appended claims.

EXAMPLES

A pharmaceutical composition was prepared per the above-described methods to evaluate the ability of an *Ambrosia maritima* extract to treat coronavirus infections.

Unless otherwise noted, a purified polar organic extract from *Ambrosia maritima* was obtained by dipping the powder of the dried whole plant material into ethanol to extract the active polar compounds such as the SLs. The mixture was allowed to set at room temperature for 2 days before filtering the plant material and collecting the extract, which contained the organic solutes. The polar organic solvent was then dried off using conventional drying methods. The presence of at least four SLs, parthenin, ambrosin, damsin, and neoambrosin, were confirmed in the organic extract. These four SLs were chemically fractionated with chloroform, wherein the fractions rich in these SLs were then pooled. The chloroform was evaporated off and the fractionated material was washed with ethanol to fully rid it of chloroform. The ethanol was then removed, leaving behind the dried, pharmaceutically active components, which is referred to as "purified polar organic extract" in the following examples. This dried purified polar organic extract was suitable for use in the following cytotoxicity and in vitro examples. It was combined with dimethyl sulfoxide (DMSO) to form a 30 vol. % solution. For the in vivo "clinical" example, 500 mg of the purified polar organic extract was combined with polyethylene glycol to form a soft gelatin capsule weighing 1.22 g. This pharmaceutical composition is referred to as Composition 1 in the Examples below.

In some of the plaque reduction assays, a composition with just the fractions rich in ambrosin and damsin were prepared. The fractionation and purification steps were the same as the purified polar organic extract, and this composition was also combined with DMSO to form a 30 vol. % solution.

Cytotoxicity Assay

The cytotoxicity of the purified polar organic extract was evaluated using serial dilutions of the purified polar organic extract, from 500 μg/ml to 15.65 μg/mL, using a 3-(4,5-Dimethylthiazol-2-yl)-2,5-diphenyltetrazolium bromide (MTT) assay.

For the MTT cytotoxicity assay ($IC_{50}$), samples were diluted with Dulbecco's Modified Eagle's Medium (DMEM). Stock solutions of the test compounds were prepared in 10% DMSO in $ddH_2O$. The cytotoxic activity of the extracts was tested in Vero E6 cells by using the MMT assay in Mosmann (1983) with minor modification. Briefly, the cells were seeded in 96 well-plates (100 μL/well at a density of 3×105 cells/mL) and incubated for 24 hours at 37° C. in 5% $CO_2$. After 24 hours, cells were treated with various concentrations of the tested compounds in triplicates. After a further 24 hours, the supernatant was discarded, and cell monolayers were washed with sterile phosphate buffer saline (PBS) 3 times. MTT solution (20 μL of 5 mg/mL stock solution) was added to each well and incubated at 37° C. for 4 hours followed by medium aspiration. In each well, the formed formazan crystals were dissolved with 200 μL of acidified isopropanol (0.04 M HCl in absolute isopropanol=0.073 mL HCL in 50 mL isopropanol). Absorbance of formazan solutions were measured at $\lambda_{max}$=540 nm with 620 nm as a reference wavelength using a multi-well plate reader (SpectraMax M5. The percentage of cytotoxicity compared to the untreated cells was determined with Equation 1. The plot of % cytotoxicity versus sample concentration was used to calculate the concentration which exhibited 50% cytotoxicity (IC50).

$$\% \text{ cytotoxicity} = \frac{(\text{absorbance of cells without treatment} - \text{absorbance of cells without treatment}) \times 100}{\text{absorbance of cells without treatment}} \quad \text{Equation 1}$$

The results are shown in Table 1 and FIG. 2.

TABLE 1

Cytotoxicity results for a purified extract from Maritima

| Concentration of Purified polar organic extract (µg/mL) | Cytotoxicity (%) |
|---|---|
| 500 | 98.894 |
| 250 | 98.894 |
| 125 | 85.806 |
| 62.5 | 55.023 |
| 31.25 | 15.207 |
| 15.65 | 8.756 |

Figure 2:
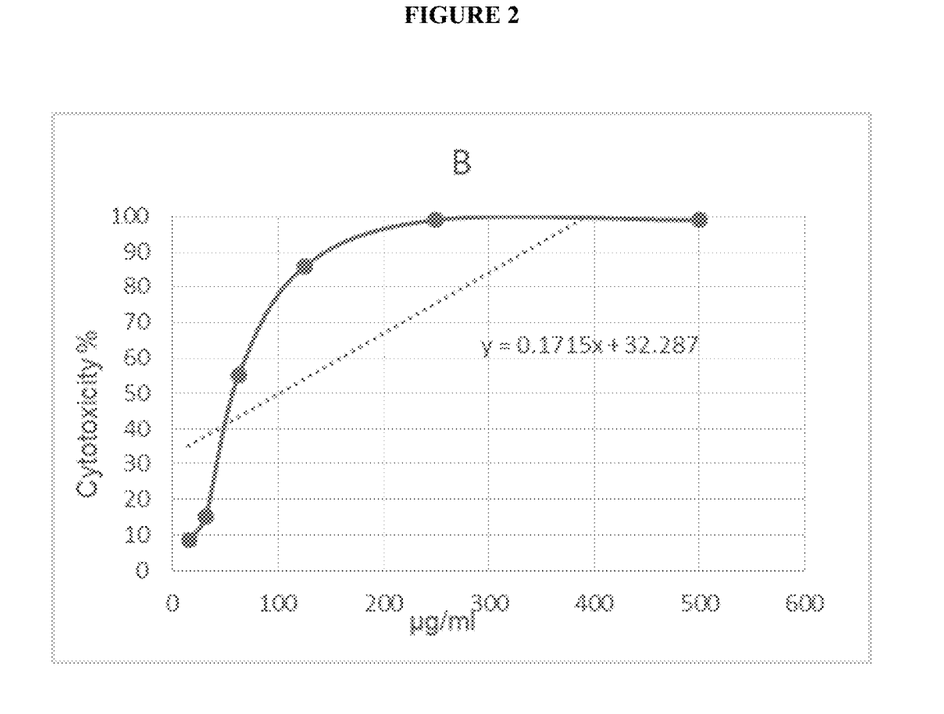
FIG. 2. Relationship between cytotoxicity (%) and concentration (µg/mL) of a purified organic extract from *Ambrosia maritima*.

The cytotoxicity varied from about from 98.894% to 8.75%. As expected, the larger concentrations of the purified extract had about 100% cytotoxicity. According to the results shown in FIG. 2, the IC50 was 103.2 µg/ml in the A549 cell lines. From these results, it was determined that the suitable concentrations for the plaque reduction test were 62.5 µg/mL, 31.25 µg/mL, and 15.65 µg/mL, as each was much lower than the IC50, indicating their lack of toxicity.

Plaque Reduction Test

Plaque reduction tests were performed to measure the presently disclosed composition's ability to inhibit a COVID-19 infection.

The plaque reduction assays were carried out according to the method of Hayden et al., 1980. The sample mixtures prepared for the plaque reduction test are as follows: A 'blank' mixture were prepared with SARS-CoV-2 (Wuhan, CN) that was diluted to give $10^5$ plaque forming units (PFU)/well. This mixture was used for the control wells (for untreated virus). For the sample mixtures, 120 µL of the diluted SARS-CoV-2 was combined with 120 µL of a purified polar organic extract from *Ambrosia maritima* having a concentration of 62.5 µg/mL, 31.25 µg/mL, 15.65 µg/mL and 7.8 µg/mL. The cells used in the present example were Vero E6 (also called Vero C1008). A growth medium for culturing the Vero E6 cells contained DMEM, 2% fetal bovine serum (FBS) and 1% of an antibiotic solution (Gibco). Additional media used in the assay included an overlayer medium consisting of 2% agarose (autoclaved) in DMEM, and a "2x medium" consisting of DMEM 2% FBS+L-glutamine+Sodium Bicarbonate.

In more detail, Vero E6 cells (also called Vero C1008) were placed in a six well plate at a concentration of 105 cells/mL, and cultivated for 24 hours at 37° C. with 5% $CO_2$. Meanwhile, the SARS-CoV-2 was diluted to give 105 plaque forming units (PFU)/well and mixed with a safe concentration of the purified polar organic extract to form the sample mixture and incubated for 1 hour at 37° C. After the incubation period, the growth medium was removed from the cell culture plates, and the cells were inoculated with 100 µL of the sample mixture per well.

After 1 hour of contact time for virus adsorption, the supernatant was then removed and the cells were washed with phosphate buffer solution (PBS) twice. Then, 3 mL of an overlayer medium (DMEM medium supplemented with 2% agarose) and 2X medium (1:1 ratio) were added onto the cell monolayer. Plates were left to solidify and incubated at 37° C. with 5% $CO_2$ until formation of viral plaques (3 to 4 days).

To fix the cells, formalin (10%) was added and, after for two hours, the plates were stained with 1.5 mL of 0.1% crystal violet (Sigma Aldrich) in distilled water. The stained cells were then analyzed for plaque reduction.

Control wells using the untreated virus (blank mixture) were also prepared, incubated with Vero E6 cells, and processed in same way. The percentage of reduction in plaques formation in comparison to the control wells was recorded as: % inhibition={viral count (untreated)−viral count (treated)/viral count (untreated)}×100. The results are shown in Table 2.

TABLE 2

Results from Plaque reduction test

| Concentration of purified polar organic extract (µg/mL) | Initial Viral count (PFU/mL) | Viral count after treatment (PFU/mL) | Inhibition (%) |
|---|---|---|---|
| 62.50 | 100 * $10^5$ | 3 * $10^5$ | 97 |
| 31.25 | | 25 * $10^5$ | 75 |
| 15.60 | | 45 * $10^5$ | 55 |
| 7.80 | | 52 * $10^5$ | 48 |

PFU = plaque forming units

The results in Table 2 show that the addition of the presently disclosed compositions decreases the viral count. As little as 7 µg/mL of the purified polar organic extract from *maritima* inhibited viral growth by 48%. Increasing the amounts of the purified polar organic extract decreased the viral infection. As just 62.5 µg/mL, an inhibition rate of 97% was observed, which is a high efficacy against COVID-19.

In addition to an extract with ambrosin, damsin, parthenine, and neoambrosin, a plaque reduction assay was also performed for a second sample that included just ambrosin and damsin rich fractions. This mixture also showed efficacy with great result in inhibiting viral replication. As little as 62.50 µg/mL inhibited viral growth by 97%. Thus, both of these SLs can be used alone or in combination with any of the other SLs, and decreases in the viral infection will still be seen.

Clinical Results

A double-blind control testing was performed on a group consisting of 104 consenting human subjects. The human subjects were both males and females, aged 18 to 45 with an average weight of 70-80 kg and height of 150-175 cm. Each subject had tested positive for COVID-19 using a PCR test.

The subjects were split into two sub-groups of 52 participants each. The first sub-group took a placebo. The second sub-group, also called the 'test' group, was treated with 500 mg of Composition 1 every 12 hours.

The test sub-group tested negative for COVID-19 after 5 days of treatment, with a cure rate of 100% after five days of treatment. It was also noted that improvements in symptoms were observed within 3 days of the first treatment with Composition 1. In contrast, all fifty-two participants in the first sub-group tested positive for COVID-19 after 5 days, and returned positive COVID-19 tests for up to 15 days.

It has been shown by the above examples that the presently described pharmaceutical compositions obtained using extracts from the *martima* plant can be used to treat coronavirus infections. However, this is exemplary only, and the invention can be broadly applied to any *Ambrosia* plant. Further, any SLs found in these plants are expected to show some level of cytotoxicity for treatment and prevention of coronavirus infections. The foregoing examples are intended to be illustrative only, and not unduly limit the scope of the appended claims.

The following references are incorporated by reference in their entirety.

Tackholm, Vivi. (1974). Student's flora of Egypt. 2nd edition, Cairo University, Egypt.

Sherif, A. F. and M. F. El-Sawy, (1977). Field trials of the Molluscicidal action of *Ambrosia maritima* (Damesisa). Bull. High Inst. Puplic Health Alex. 7:1-4.

El Sawy M F, El Hamd Z M S, Loutfy N F, El Masry S and Abdel Gualil M Z (1986): J of the Egypt. Society of Parasitology, 16:1, pp 57-64.

Abdallah, O. M.; Ali, A. A. and Itokawa, H. (1991). "Cytotoxic activity of Sesquiterpene lactones isolated from *Ambrosia maritima*". Pharmazie, 46(6):472.

Badawy, M.; Abdelgaleil, S. A. M.; Suganuma, T. and Fuji, M. (2014). "Antibacterial and biochemical activity of Pesudoguaianolide Sesquiterpene isolated from *Ambrosia maritima* against plant pathogenic bacteria". Plant protect. Sci. 50 (2): 64-69.

Hayden, F. G.; Cote, K. M. and Douglas Jr, R. G. (1980). "Plaque inhibition assay for drug susceptibility testing of influenza viruses", Antimicrobial Agents and Chemo., 17 (5): 865-870.

Mosmann T (December 1983). "Rapid colorimetric assay for cellular growth and survival: application to proliferation and cytotoxicity assays". Journal of Immunological Methods. 65 (1-2): 55-63.

The invention claimed is:

1. A method of treating a coronavirus infection, comprising administering an effective amount of a composition comprising a polar organic extract of a whole Ambrosia maritima plant together with a pharmaceutically acceptable carrier to a patient with a coronavirus infection, wherein the coronavirus infection is SARS-CoV-2 infection.

2. The method of claim 1, wherein said effective amount is administered daily for at least 5 days.

3. The method of claim 1, wherein said polar organic extract comprises at least one sesquiterpene lactone.

4. The method of claim 1, wherein said polar organic extract comprises one or more of the following sesquiterpene lactone: parthenin, ambrosin, damsin, and neoambrosin.

5. The method of claim 1, wherein said polar organic extract comprises parthenin, ambrosin, damsin, and neoambrosin.

6. The method of claim 1, wherein said patient is human, non-human primate, cat, dog or mink.

7. A method of treating a coronavirus infection, comprising administering an effective amount of a composition comprising sesquiterpene lactones extracted from a whole Ambrosia maritima plant together with a pharmaceutically acceptable carrier to a patient with a coronavirus infection, wherein the coronavirus infection is SARS-CoV-2.

8. The method of claim 7, wherein said effective amount is administered daily for at least 5 days.

9. A method of treating a coronavirus infection in an animal, said method comprising daily administration of an effective amount of a pharmaceutical preparation comprising parthenin, ambrosin, damsin, and neoambrosin plus a pharmaceutically acceptable excipient to said animal for at least 5 days, wherein the coronavirus infection is SARS-CoV-2.

10. A method of treating a coronavirus infection, comprising:
   a) preparing a sesquiterpene lactone-containing extract comprising the steps of:
      i) treating a whole plant of Ambrosia maritima with a polar organic solvent in which one or more sesquiterpene lactones is soluble;
      ii) evaporating the polar organic solvent to produce a crude extract;
      iii) subjecting the crude extract to chromatography using a second organic solvent to obtain a purified extract of said one or more sesquiterpene lactones;
      iv) collecting fractions of the individual one or more sesquiterpene lactones to form said sesquiterpene lactone-containing purified extract from step a)-iii); and,
   b) adding a pharmaceutically acceptable carrier to said sesquiterpene lactone-containing extract to form a pharmaceutical composition; and,
   c) administering an effective amount of said pharmaceutical composition to a patient with a coronavirus infection;
   wherein the coronavirus infection is SARS-CoV-2.

* * * * *